United States Patent [19]
Hara et al.

[11] Patent Number: 4,946,950
[45] Date of Patent: Aug. 7, 1990

[54] INOSITOL GLYCOSIDE 2-O-BETA-L-ARABINOPYRANOSYL-MYO-INOSITOL

[75] Inventors: Yukihiko Hara; Kazuo Okushio, both of Shizuoka; Kanzo Sakata, Shimizu, all of Japan

[73] Assignee: Mitsui Norin Co., Ltd., Tokyo, Japan

[21] Appl. No.: 153,850

[22] Filed: Feb. 8, 1988

[30] Foreign Application Priority Data

Feb. 23, 1987 [JP] Japan .................................. 62-37726

[51] Int. Cl.$^5$ ...................... C07H 15/20; A61K 31/70
[52] U.S. Cl. .................................................... 536/4.1
[58] Field of Search ...................... 536/4.1; 514/25, 35

[56] References Cited

PUBLICATIONS

Ueda et al; Chemical Abstracts, 74:72808v (1971).
Derappe et al; Carbohydr. Res. 115:221–229 (1983).
Meyer et al; FEBS Lett. 172(1):99–102 (1984).
Stepanov et al; Chemical Abstracts 85:63298d (1976).
Garegg et al; Carbohydr. Res. 139:209–215 (1985).
Sakata et al; Agric. Biol. Chem. 51(6):1737–1739 (Jun. 1987).

Primary Examiner—Ronald W. Griffin
Assistant Examiner—Nancy S. Carson
Attorney, Agent, or Firm—Frishauf, Holtz, Goodman & Woodward

[57] ABSTRACT

A glycoside of inositol which has been isolated from a hot-water extract of tea leaves. The glycoside is identified from the analytical results to be 2-O-beta-L-arabinopyranosyl-myo-inositol.

2 Claims, 4 Drawing Sheets

INOSITOL GLYCOSIDE 2-O-BETA-L-ARABINOPYRANOSYL-MYO-INOSITOL

BACKGROUND OF THE INVENTION

The present invention relates to a novel inositol glycoside or, more particularly, to an inositol glycoside extractable from tea leaves designated 2-O-beta-L-arabinopyranosylmyo-myo-inositol, referred to hereinbelow as the novel inositol glycoside.

As an important product in the agriculture and food industry, tea leaves have been extensively analyzed and various kinds of chemical compounds have been reported as the characteristic constituents thereof. The present invention resulted from studies to determine constituents of tea leaves. The novel inositol glycoside which is the present invention was first discovered as a result of these studies and was determined to have certain unique properties making it particularly valuble in the beverage industry.

The novel inositol glycoside of the present invention is a crystal white substance without noticeable taste. It is neither sweet nor bitter. However, an aqueous solution at beverage concentrations imparts the same "mouthing" or "mouthfeel" to the palate as does sugar and when sugar is used at usual beverage or "soft drink" concentrations. This allows one to formulate a "soft drink" beverage to give the "feel" o "mouth" of sugar without sweetness: that is, it gives a certain anticipated mouthfeel such as one expects from sugar (without sweetness) and it is not sticky or glutinous as is usual with other sugar substituting saccharides. Moreover this new glycoside is believed to be essentially indigestible in humans since it is unassimilable by many microorganisms.

The properties of this new glycoside give it wide applicability in the food beverage and pharmaceutical industries. For example, sugar decays the teeth and increases cholesterol. To avoid these disadvantages, sugarless beverage formulation are usual, for example sugarless cola. But consumers are not happy without sweetness and expected "mouthfeel". Adding a sugarless artificial sweeter would solve the problem of sweetness; however artificial sweetness does not give the right "mouthfeel". This deficiency can be solved with the inositol glycoside of the invention. The result is healthy teeth and moderate cholesterol level with satisfactory drinks. Many confectioneries have the same problem. The same is true for pharmaceutical formulations. The invention is therefore useful in many fields.

Commercially, syrups of various fruit flavors, teas, and coffees are prepared for vending and catering trade. Their sugar or inverted sugar content is at least about 60% by weight to avoid yeast or bacterial growth. They are then diluted 6-7 times at the consuming end to give products with acceptable mouthfeel. The problem is that even with 7 times dilution with water modern consumers feel that the flavor is too sweet. Again there is no suitable saccharides. In this case sweetness is reduced by substituting the inositol glycoside for sugar, keeping both the "mouthfeel" and yeast preventive level of water activity as it was.

Because it does not promote tooth decay, the novel inositol glycosides of the invention also have applicability in oral care products such as "mouthwashes" or "rinses". Pleasant "mouthfeel" can be imparted to these products without the ill effects of sugar.

SUMMARY OF THE INVENTION

The present invention provides the inositol glycoside, 2-O-beta-L-arabinopyranosyl-myo-inositol which has the following structural formula:

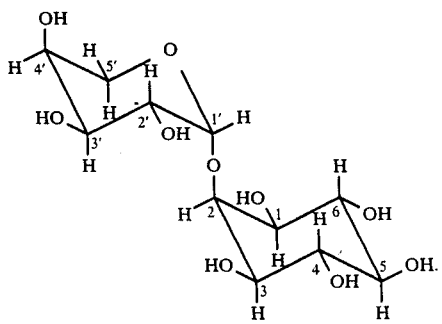

DETAILED DESCRIPTION OF THE INVENTION

The appearance of the novel inositol glycoside of the invention is white or colorless transparent rodlike crystals, without taste or odor. The compound is characterized by the following properties.

Melting point: the compound is crystallized in two different crystalline forms having different melting points, one, in the range from 196° to 198° C. and, the other, in the range from 225.5° to 227.5° C. The chemical identity of these two different crystalline forms was confirmed by the elementary analysis, NMR analysis and other methods. It was noted in the course of temperature elevation that the compound apparently sintered at about 140° C.

Elementary analysis: the analysis of a purified standard specimen determined 41.96% of C and 6.44% of H which is in good agreement with calculated values of 42.31% of C and 6.46% of H for $C_{11}H_{20}O_{10}$.

Thin-layer chromatography: Rf=0.20 (Rf relative to quinic acid=0.74) using a silica gel $CF_{254}$ (Merck) and a 12:3:3:2 mixture of ethyl acetate, methyl alcohol, acetic acid and water as the eluant.

Figure 1:
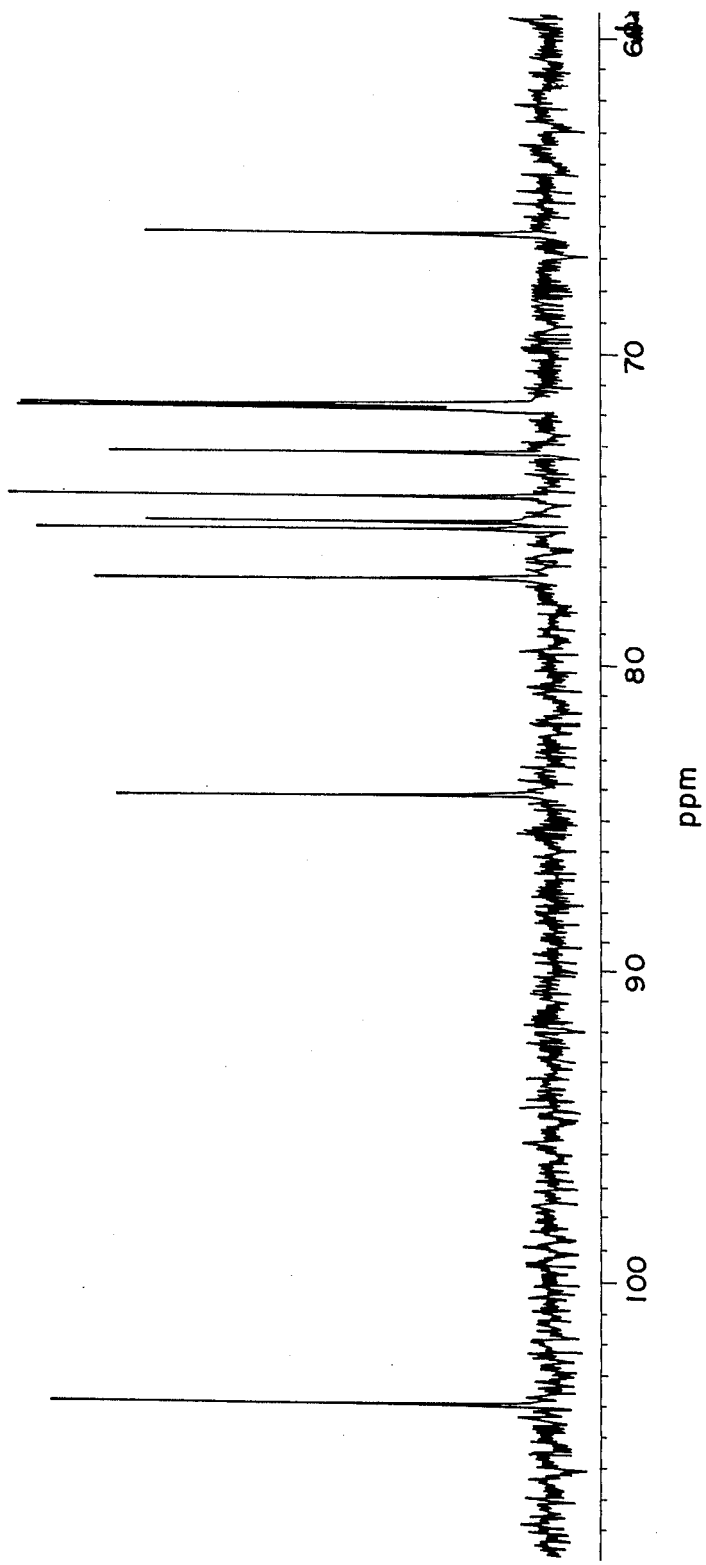
FIG. 1 is a $^{13}$C-NMR absorption spectrum of the inositol glycoside of the invention.

$^{13}$C-NMR: ($D_2O$, TSP-$d_4$, 101 MHz) see FIG. 1. δ: 66.23 (t); 71.66 (d); 71.74 (d); 71.85 (d); 73.27 (d); 74.71 (d); 75.50 (d); 75.76 (d); 77.31 (d); 84.23 (d); and 104.0 (d, J=170 MHz)

Figure 2:
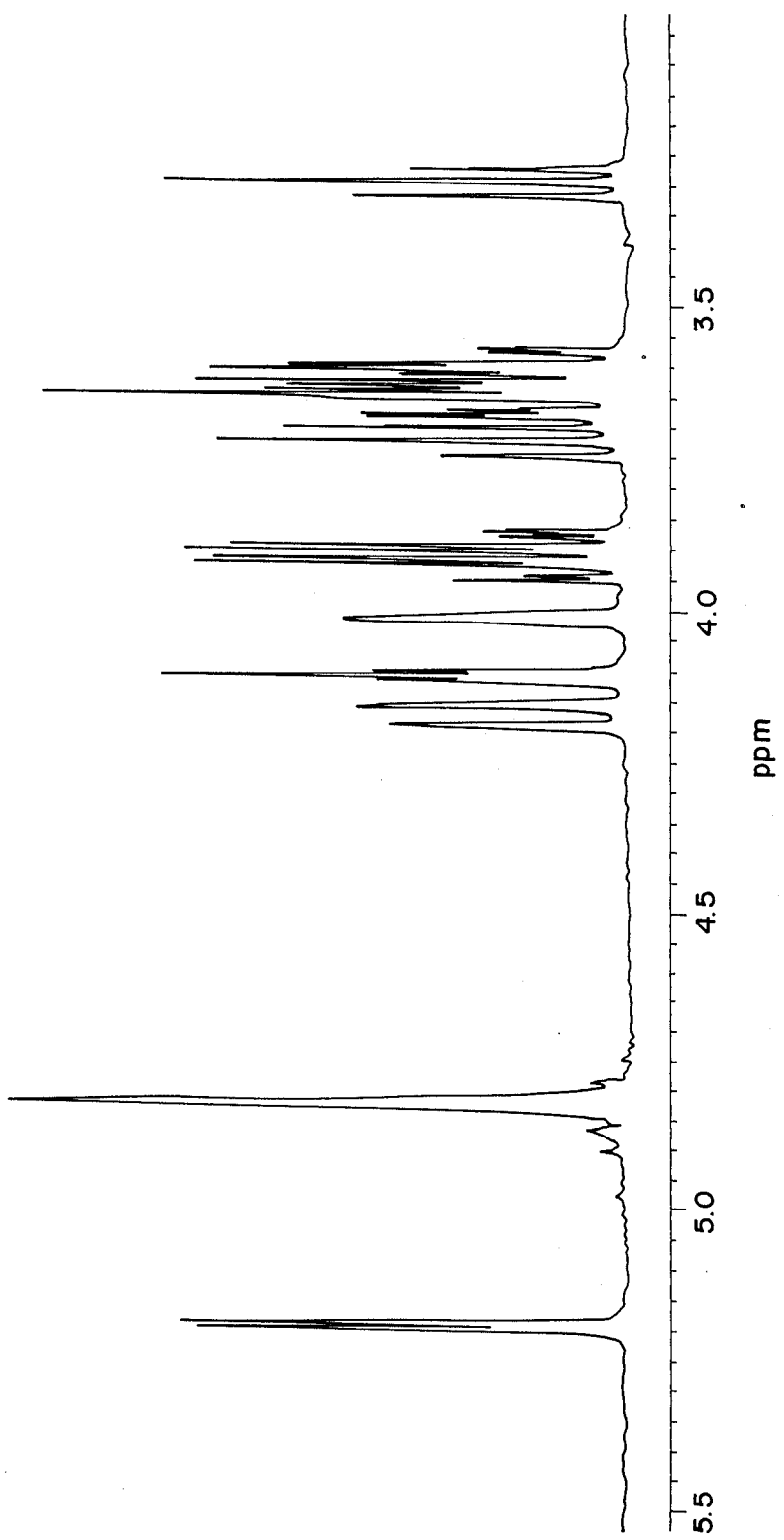
FIG. 2 is a $^1$H-NMR spectrum of the inositol glycoside.

$^1$H-NMR: ($D_2O$, TSP-$d_4$, 400 MHz) see FIG. 2. δ: 3.29 (1H, t, 9.2); 3.59 (1H, dd, 10, 2.5); 3.62 (1H, dd, 10, 2.4); 3.64 (1H, t, 9.5); 3.66 (1H, dd, 13, 2.4); 3.72 (1H, t, 9.5); 3.89 (1H, dd, 10, 3.4); 3.93 (1H, dd, 10, 3.1); 4.02 (1H, broad, s, $W_\frac{1}{2}$=6.8); 4.11 (1H, t, 2.5); 4.17 (1H, dd, 13, 1.2); and 5.19 (1H, d, 3.4)

FD-MS: m/z (relative intensity) 351 (M+K, 100); 335 (M+Na, 2); 269 (10); 156 (4); 122 (5) and 104 (5)

Figure 3:
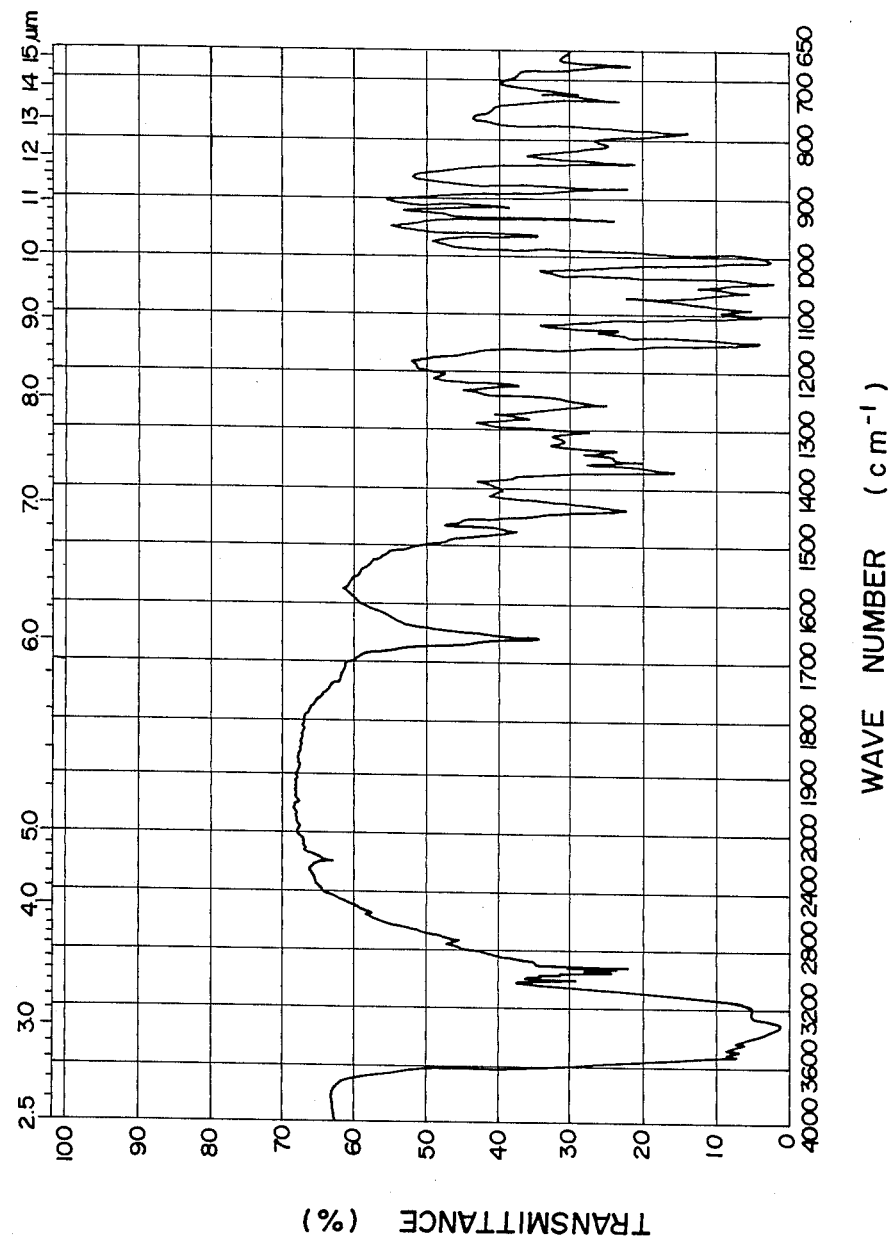
FIG. 3 is an infrared absorption spectrum of the same compound.

Infrared absorption spectrum: see FIG. 3 (KBr tablet method).

The novel inositol glycoside is contained in various kinds of tea leaves including fresh tea leaves, green tea as well as instant green tea, black tea as well as instant black tea, oolong tea, pu-erh tea and the like. The content of the compound in dry tea leaves is usually from about 0.5% by weight to about 1% by weight. The content of the novel inositol glycoside is relatively high in the so-called pu-erh tea which is prepared by 1 to 3 years of aging of a Chinese tea after inoculation with fungi. This fact indicates that the compound of the present invention is substantially unassimilable by microorganisms because the compound survives the aging with fungi and remains in the pu-erh teas while ordinary saccharide compounds contained in tea leaves are readily metabolized by fungi.

The novel inositol glycoside can be obtained by extraction from tea leaves by the following process:

Tea leaves of a desired grade are extracted with hot water.

Figure 4:
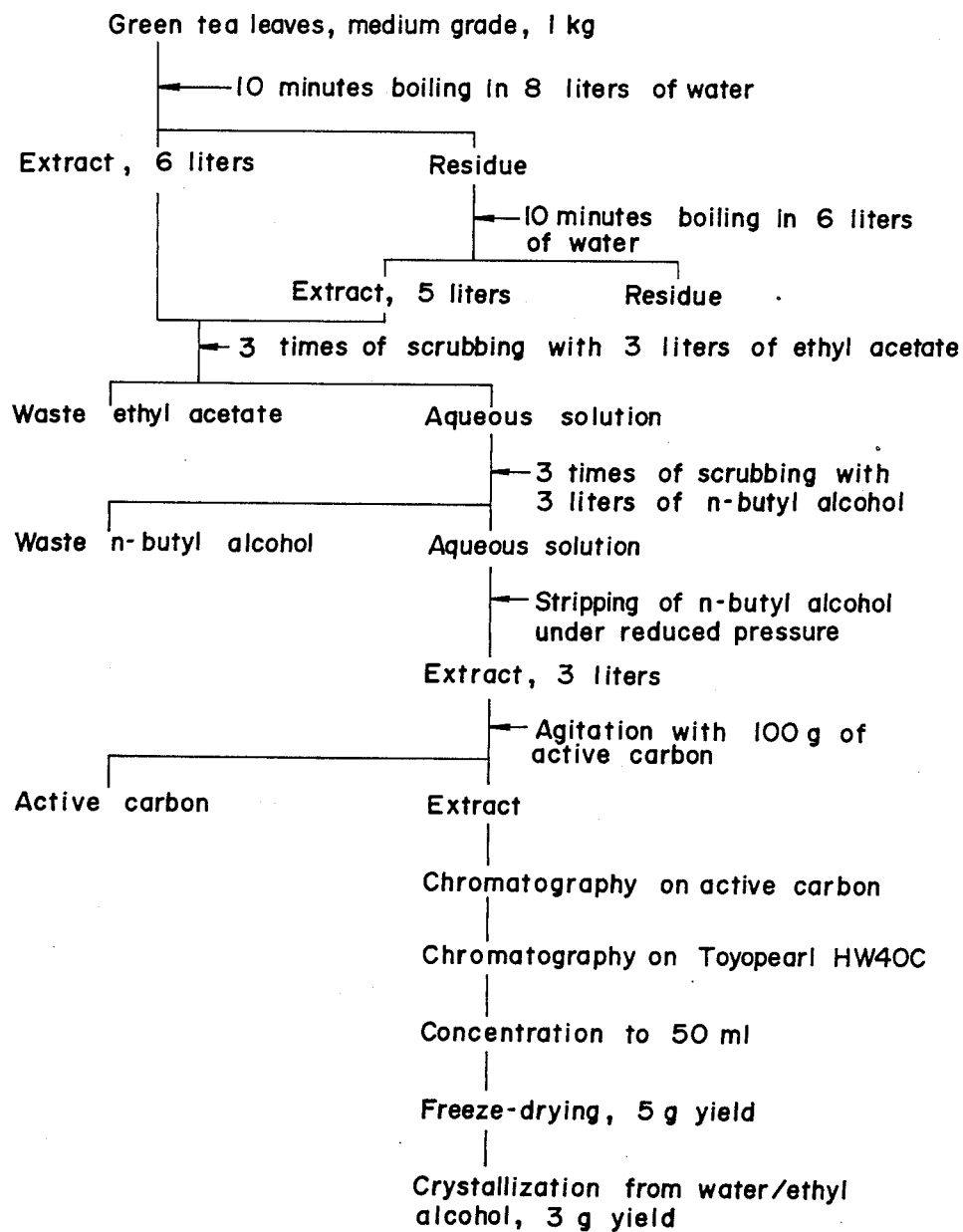
FIG. 4 is a typical flow diagram showing the process of isolation of the novel inositol glycoside from tea leaves.

The water extract is washed with an organic solvent such as ethylacetate, n-butyl alcohol and the like. Thereafter, the washed extract is contacted or treated with active carbon. The active carbon is removed and the extract is then fractionated by a chromatographic method. The fraction containing the compound is then concentrated and freeze-dried to isolate the compound. If desired, the thus obtained product may be purified by recrystallization. FIG. 4 shows a typical flow diagram showing the process of isolation of the novel inositol glycoside from tea leaves.

Besides the above mentioned extraction method from tea leaves, the novel inositol glycoside of the invention, having a well defined chemical structure, can be prepared by a usual organo chemical synthesis method or by usual enzymatic methods. Microbiological fermentation methods are also applicable to the preparation of the novel inositol glycoside.

To summarize, the novel inositol glycoside of the invention is contained in tea leaves in general and is characteristically hardly assimilable by microorganisms such as fungi in contrast to the ordinary saccharide compounds contained in tea leaves which are metabolized by fungi. In addition, the novel inositol glycoside is a kind of saccharide compound having no sweet taste although it can impart favorable mouthing characteristics so that it has usefulness in various fields such as food industries, pharmaceutical industries and the like.

In the following, the novel inositol glycoside and the method for the preparation thereof are described in more detail by way of an example.

EXAMPLE 1

According to the procedure illustrated by the flow chart given in FIG. 4, 1 kg of green tea of medium grade was subjected successively to extraction with hot water, washing with organic solvents, treatment with active carbon, chromatography on active carbon, chromatography on Toyopearl HW40C, concentration by evaporation of the solvent and freezedrying to give 5 g of the novel inositol glycoside which was purified by crystallization from water/ethyl alcohol to give 3 g of the glycoside in a crystalline form.

The same procedure as above was repeated excepting replacement of 1 kg of the green tea of medium grade with each 1 kg of black tea, oolong tea and pu-erh tea to give 3 g, 4 g and 5 g, respectively, of the novel inositol glycoside after crystallization.

Application example 1

Sucrose is considered to be one of the main factors of tooth decay. Dextran, produced from sucrone by *Streptococcus mutance*, covers the tooth surface and inside, acids, produced also from sucrose by *S. mutance* and others, decay the tooth. The inositol glycoside of this invention was tested if this is metabolized by *Streptococcus mutance* to produce either acids or dextran to cause tooth decay.

| PYP Medium (pH 7.2) | |
|---|---|
| Peptone | 0.5 g |
| Yeast Extract | 0.5 g |
| NaCl | 5.0 g |
| $K_2HPO_4$ | 0.3 g |
| Agar | 3.0 g |
| Phenol Red | 0.02 g |
| Water | 1000 ml |
| 10% Saccharide Solution | |

4.5 ml of PYP medium and 0.5 ml of 10% saccharide solution were mixed and *S. mutance* were incubated in this mixed medium for 7 days at 30° C.

When the saccharide was sucrose the medium turned yellow by the acid produced and also became turbid by the growth of the bacteria. Whereas when the saccharide was the inositgl glycoside of this invention the color of the medium remained red and transparent. These facts show that the inositol glycoside were neither metabolized nor produce acid by *S. mutance*.

Application example 2

In order to confirm that the inositol glycoside does not cause tooth decay, another test was conducted. The broth medium below is a dextran forming medium.

| [a] (pH 7.0) | |
|---|---|
| Beef Ext. | 20 g |
| Peptone | 20 g |
| NaCl | 10 g |
| $K_2HPO_4$ | 5 g |
| Yeast Ext. | 4 g |
| Water | 1000 ml |
| [b] 2% Saccharide Solution | |

[b] 2% Saccharide Solution

Both 7.5 ml of [a] and [b] were mixed in a test tube with a glass rod inside and *Streptococcus mutance* were incubated under anaerobic condition for seven days at 30° C.

When the saccharide solution of [b] was made of sucrose, the glass rod as well as tube wall were covered with moss like substance. Whereas when the saccharide was the inositol glycoside both the glass rod and the tube wall remained clean. This fact indicates that dextran is very unlikely to be formed by the inositol glycoside.

What is claimed is:

1. A glycoside of inositol which is substantially pure 2-O-beta-L-arabinopyranosyl-myo-inositol expressed by the structural formula:

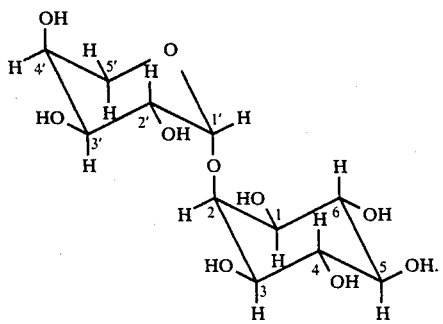
2. A glycoside of inositol according to claim 1 which is crystallized 2-O-beta-L-arabinopyranosyl-myo-inositol expressed by the structural formula:
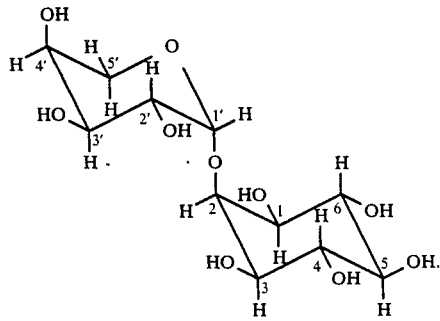
* * * * *